United States Patent [19]

Joa

[11] 4,307,800
[45] Dec. 29, 1981

[54] APPARATUS FOR ALTERNATING THE FOLDED AND OPEN EDGES OF A SUCCESSION OF FOLDED PADS

[76] Inventor: Curt G. Joa, P.O. Box 1121, Boynton Beach, Fla. 33435

[21] Appl. No.: 99,291

[22] Filed: Dec. 3, 1979

[51] Int. Cl.³ .................... B65G 47/24; B65G 57/32
[52] U.S. Cl. ............................ 198/374; 198/422; 271/65; 271/186; 271/DIG. 10; 271/302; 414/31; 414/55
[58] Field of Search .................. 198/374, 420, 422; 270/58; 271/65, 186, DIG. 9, DIG. 10, 302; 414/31, 30, 55; 53/143, 544

[56] References Cited

U.S. PATENT DOCUMENTS

| 2,324,930 | 7/1943 | Joa | 271/DIG. 10 X |
| 3,391,777 | 7/1968 | Joa | 198/422 |
| 3,593,624 | 7/1971 | Dufour | 414/31 X |

FOREIGN PATENT DOCUMENTS

| 917764 | 9/1954 | Fed. Rep. of Germany ... 271/DIG. 10 X |
| 2438811 | 2/1976 | Fed. Rep. of Germany ...... 198/374 |
| 1496243 | 12/1977 | United Kingdom .................. 271/65 |

*Primary Examiner*—Bruce H. Stoner, Jr.
*Attorney, Agent, or Firm*—Wheeler, House, Fuller & Hohenfeldt

[57] ABSTRACT

A succession of pads such as disposable diapers, all folded in the same direction originally, are received in an oscillating conveyor which directs alternate pads into separate lanes. The first lane has orbiting paddles for receiving pads folded in their original direction and for inverting them to reverse their fold direction. A conveyor transports the inverted pads to a collection table. The second lane has cooperating conveyor belts for transporting pads, having their folded edges in the original orientation, to the collection table for being stacked on top of a coincidentally arriving inverted pad from the first lane.

1 Claim, 3 Drawing Figures

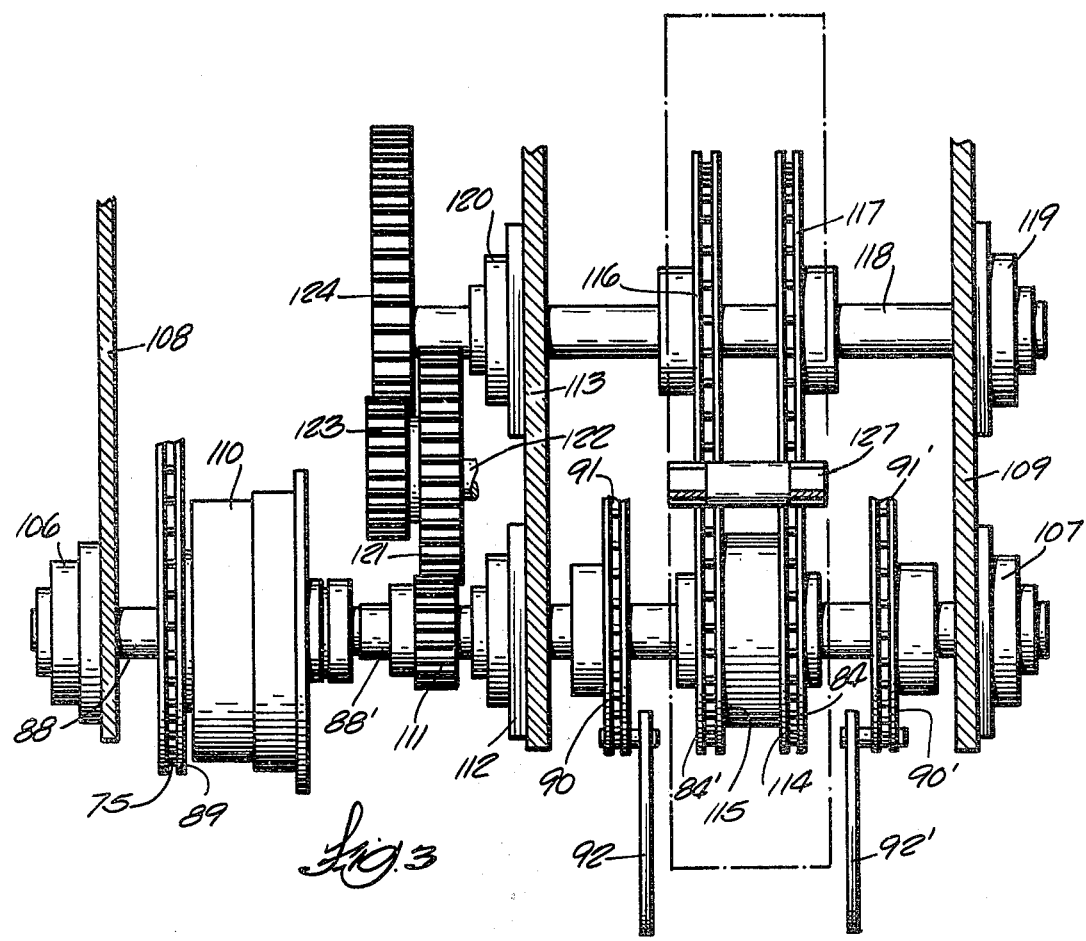

APPARATUS FOR ALTERNATING THE FOLDED AND OPEN EDGES OF A SUCCESSION OF FOLDED PADS

This disclosure relates to apparatus for enabling folded pads, such as disposable diapers, to be stacked in a stable and compact manner.

As is well-known, disposable diaper pads have multiple layers including a fluid impermeable flexible backing sheet, a mass of fine fluid absorbing fibers on the backing sheet and a top sheet of fluid permeable material which is adhered to the edges of the backing sheet and interfaces with the body of the infant on which the diaper is used. Usually the diapers are folded on their midline at the output stage of the diaper manufacturing machine to prepare the diapers for being packaged. All diapers come out of the folding stage folded in the same direction, that is, with all of their folded edges leading and their open or free edges trailing or vice versa.

It has been customary to stack and package diapers in the same orientation they have when they are discharged from the folding stage. This results in all of the folded edges being on one side of the stack and all of the free or open edges being on the other side. Folding causes the total thickness of the two halves of the diaper to be greater where the fold occurs than in other parts of the diaper which extend from the fold to the free or open edges. Applying any significant pressure on the diaper to achieve a sharp fold would result in undesirable compacting of the soft materials out of which the diaper is fabricated. Hence, if the diapers are stacked or packaged with all folded edges and free edges congruent, respectively, the side of the stack which has the repeatedly superimposed folds has a tendency to develop a height greater than the opposite open edge side. This condition prevents minimization of the height of the packaged diaper stack and can result in distorted, unstable and unattractive packages.

SUMMARY OF THE INVENTION

An object of the present invention is to overcome the above-noted problems by providing apparatus which inverts alternate diapers in a succession of similarly folded diapers so one diaper will have its folded edge leading and the next one will have its folded edge trailing so the diapers can be stacked in this order.

In accordance with a preferred embodiment of the invention, diapers which are all folded in the same direction are admitted to an oscillating conveyor which directs every other diaper from the succession into a different lane. The first lane has a conveyor for transporting diapers, which are folded in their original direction, to a receiving table. The second lane has a conveyor for accepting diapers folded in their original direction from the oscillating conveyor and for transporting them to an inverter. The inverter has a plurality of paddles which orbit on a power driven chain in such manner that the open or unfolded edges of the diaper, which were formerly trailing, become the leading edges when they are discharged from the inverter. The inverted diapers are conveyed to the receiving table where they arrive essentially simultaneously with diapers from the first lane. The diapers from both lanes are superimposed or stacked on the receiving table and may be taken off in pairs in which the folded edge of one diaper is on one side of the stack and the folded edge of the other is on the other side of the stack.

A more detailed description of a preferred embodiment of the invention will now be set forth in reference to the drawings.

DESCRIPTION OF THE DRAWINGS

FIG. 3 is a section taken along line 3—3 in FIG. 1.

DESCRIPTION OF A PREFERRED EMBODIMENT

Figure 1:
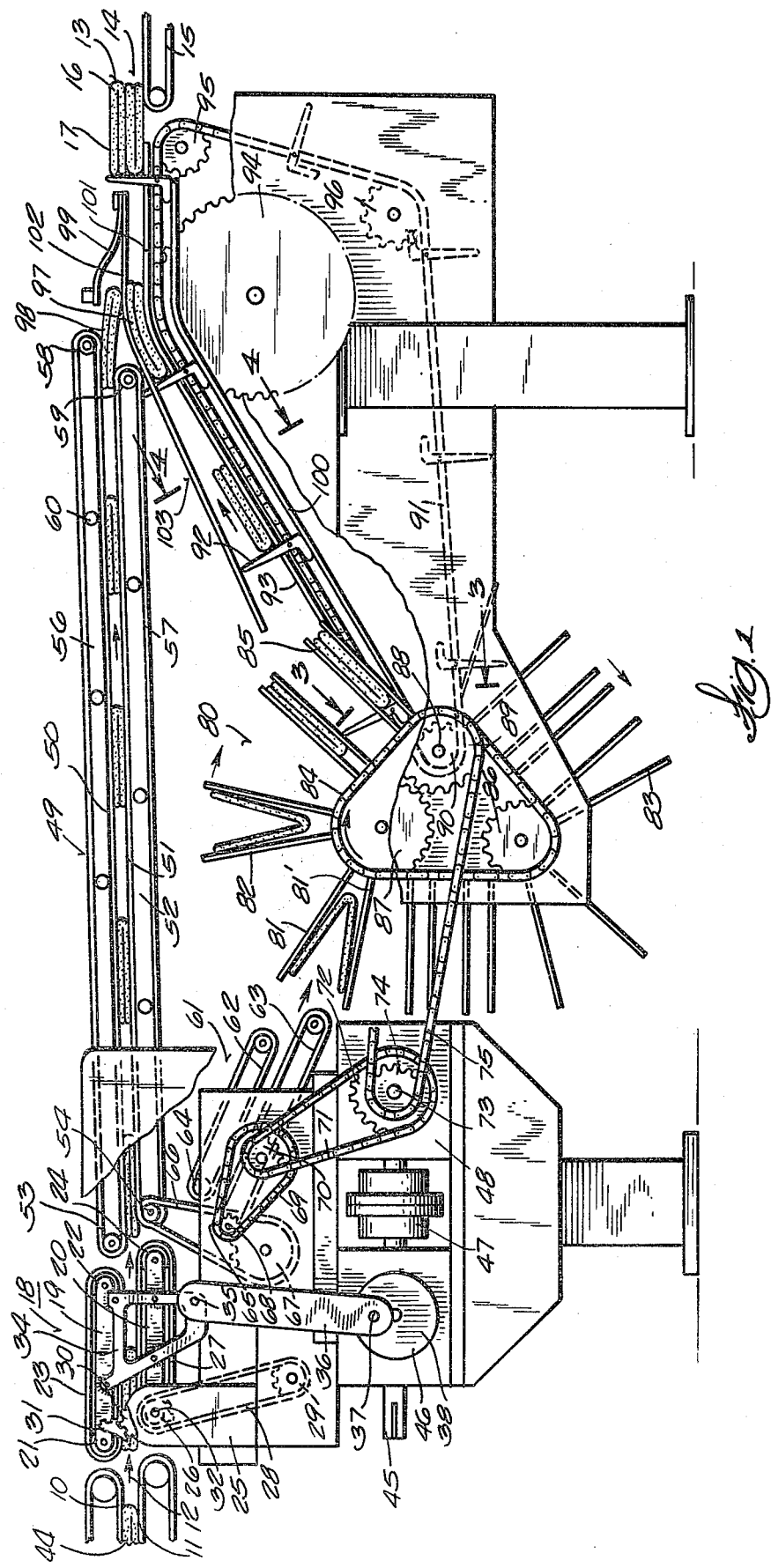
FIG. 1 is a side elevation view of the essential components of the new apparatus for alternating the folded and open edges of a succession of folded pads.

Referring to FIG. 1, a succession of similarly folded diapers are fed into the new inverting apparatus from between a pair of interfacing conveyor belts 10 and 11 which are shown fragmentarily at the far left region of this figure. The diapers travel in the direction of the arrowheaded line 12. The upper right region in FIG. 1 shows that, after going through the apparatus, two consecutive diapers 13 and 14 in the original succession are transferred in alternatingly folded pairs to an output conveyor belt 15 and then to a packaging machine, not shown. The folded edge 16 of diaper 13 is leading or on the right side of the stacked pair while its unfolded or open edges 17 are trailing and are on the left side of the stack. Diaper 14, on which diaper 13 is superimposed, is reversely oriented, that is, its open edges are on the right side of the stack and its folded edge is on the left side.

An oscillating or reciprocating conveyor, designated generally by numeral 18 in the left region of FIG. 1, constitutes the input or sorting stage of the apparatus and is operative to sort or direct alternate diapers of the incoming succession into first and second lanes, respectively. Oscillating conveyor 18 comprises rigid support members 19 and 20. Member 19 has a pair of spaced apart pulleys 21 and 22 journaled on it and a conveyor belt 23 runs on these pulleys. Support member 20 also has a pair of pulleys journaled on it, one of which is marked 24 and is visible, and the other of which is carried on a shaft 32 which is journaled in an upright bracket 25 and has a sprocket 26 fastened to it. Support members 19 and 20 are adapted to swing or pivot jointly about the axis of shaft 32 as will be further discussed later. A conveyor belt 27 runs on pulley 24 and its counterpart in spaced relationship to conveyor belt 23 for accommodating a folded diaper between them. Sprocket 26 is driven by a chain 28 from a drive sprocket 29. On the same shaft with sprocket 26 there is a gear 30 which drives a fragmentarily shown gear 31. Gear 31 is fastened to the shaft of conveyor belt pulley 21. It will be evident that when chain 28 is driven, the interfacing sides of conveyor belts 23 and 27 will translate in the same direction and transport a folded diaper captured between them to the right.

The two conveyor belt support members 19 and 20 are interconnected with a rigid generally triangularly shaped link 34. This link is pivotally connected by means of a crank pin 35 to a crank arm 36. Crank arm 36 is pivotally and eccentrically connected by means of a crank pin 37 to a power driven crank wheel 38. Rotation of crank wheel 38 causes the conveyor belt support members 19 and 20 to swing cyclically about the axis of shaft 32 between a horizontal attitude in which the members are shown in FIG. 1 to an angulated attitude in which they are shown in solid lines in FIG. 2. Pivoting of the interconnected conveyor belt support members 19 and 20 occurs around the axis of the shaft 32 which supports sprocket 26 and is journaled in bracket 25.

Figure 2:
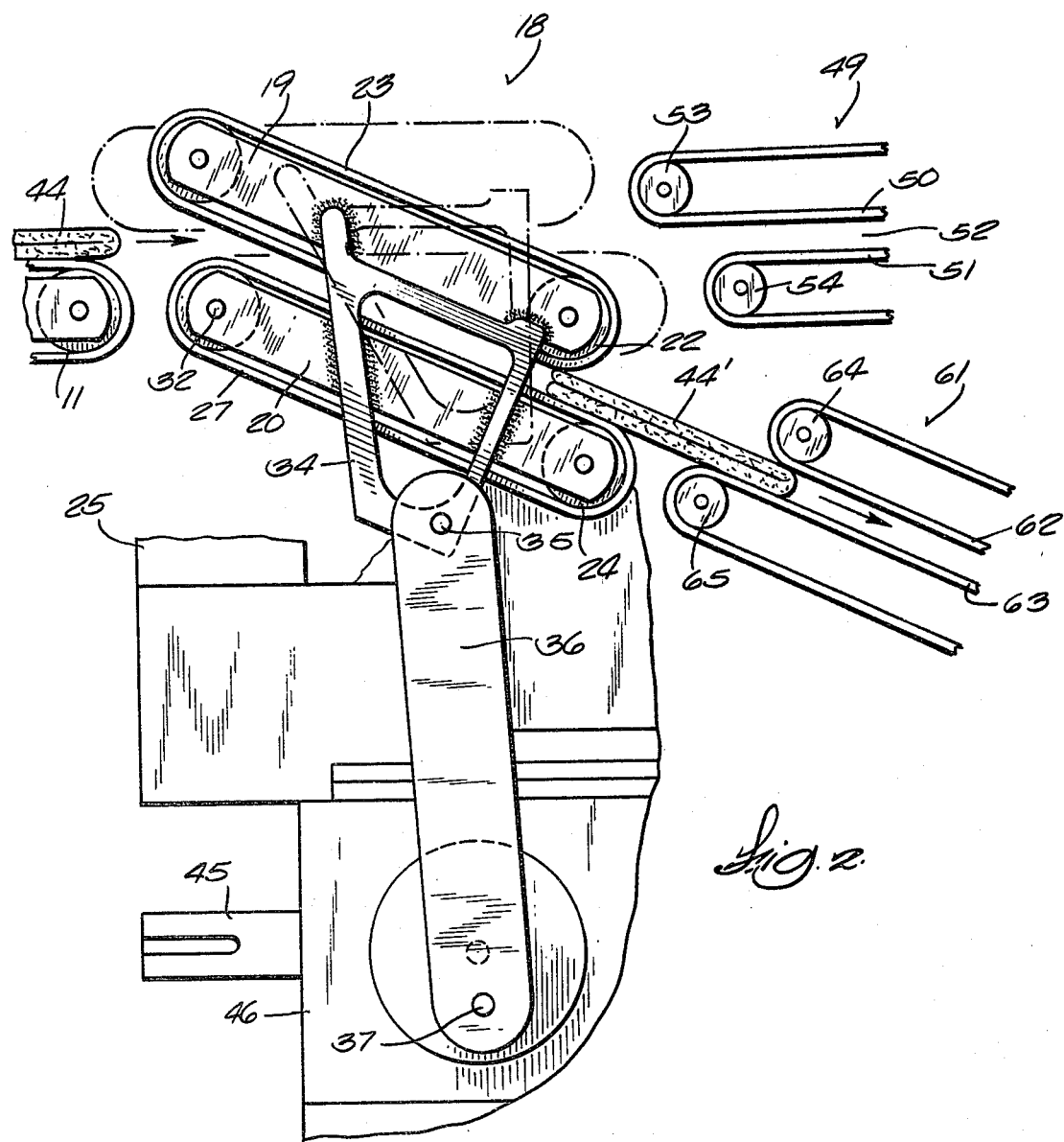
FIG. 2 is an enlarged view of a reciprocating or oscillating conveyor which has been isolated from the FIG. 1 apparatus.

In FIG. 2, conveyor belts 23 and 27 are represented in their pivoted or angulated position in solid lines and, in their unangulated positions in dash-dot lines. When belts 23 and 27 are angulated and translating as in FIG. 2, an incoming folded diaper such as the one marked 44 will be admitted between the belts and transported and discharged as is happening to the diaper marked 44'. It will be evident in FIG. 2 that diapers will be discharged into a first lane when the oscillating conveyor belts are running horizontally and that diapers will be discharged into a second lane when the oscillating conveyor is angulated. The oscillation timing is such that every other diaper in the succession of diapers coming in on input conveyor belt 11 will be directed to alternate lanes. Hence, oscillating conveyor 18 must run synchronously with diaper feed conveyor belt 11 and the diaper fabricating machine, not shown. Synchronization is accomplished by having everything driven from a common main drive shaft, not shown, that couples with the power input shaft 45 to gear box 46 as can be seen in FIG. 2. As is evident in FIG. 1, power for turning crank arm 38 is derived from gear box 46. FIG. 1 shows that shaft 45 is also extended through a coupling 47 into a gear box 48 from which power is derived for operating other components of the apparatus.

As shown in FIGS. 1 and 2, the first lane comprises a conveyor assembly 49 including a pair of conveyor belts 50 and 51 which run in parallelism and define a folded diaper accommodating space 52 between them. Conveyor belt 50 runs on pulleys 53 and 58 and belt 51 runs on pulleys 54 and 59. Belts 50 and 51 transport noninverted diapers, that is, diapers with their folded edges leading, from the oscillating conveyor 18 to the place where a noninverted diaper is superimposed on an inverted diaper.

Referring to FIG. 1, one may see that the first lane conveyor assembly 49 comprises frame members 56 and 57 whose mounting means are not shown. A pair of pulleys 53 and 58 for belt 50 are journaled on the frame member 56 and a pair of pulleys 54 and 59 for belt 51 are journaled on frame member 57. The belts are prevented from sagging with a plurality of pins, such as the one marked 60, which project from the frame members 56 and 57 into the space between opposite runs of the conveyor belt loops. Belts 50 and 51 are driven translationally to the right for transporting folded diapers to the right in FIG. 1 as a result of driving pulley 54 rotationally by means of a drive chain 66. There is a sprocket, not visible, on the shaft of pulley 54 for the drive chain 66. Chain 66 is driven from a sprocket 67 on a shaft which is suitably journaled for rotation. Sprocket 67 is driven by a gear, not visible, on a shaft which carries a small sprocket 68 and one of the pulleys 65 of a transfer conveyor 61 which will soon be described. Sprocket 68 is driven with a chain 69 from a large sprocket which is on the same shaft as a small sprocket 70. Sprocket 70 is driven by a chain 71 running on a power driven sprocket 72. Sprocket 72 is on a shaft 73 which is driven from gear box 48. There is a small sprocket 74 also fastened to shaft 78 for driving a chain 75 which is part of a diaper inverter that is soon to be described. It will be evident that conveyor belts 62 and 63 of the transfer conveyor 61 will run in synchronism with oscillating conveyor 18 and the diaper fabricating machine since they are all driven indirectly from main power shaft 45.

The second lane in FIG. 2 begins with the transfer conveyor which is designated generally by the reference numeral 61 and comprises a pair of parallel running conveyor belts 62 and 63 which run on pulleys 64 and 65, respectively. Belts 62 and 63 have a space between them for accommodating and transporting a diaper such as the one marked 44' in FIG. 2.

Referring to FIG. 1, the second lane continues from transfer conveyor 61 to a diaper inverting mechanism which is generally designated by the reference numeral 80. It comprises a plurality of paddles such as those marked 81, 82 and 83. These paddles are hingedly connected to a pair of laterally spaced chains such as the one marked 84. Translation of chain 84 results in the series of paddles following a closed loop path. It will be evident that diapers which are ejected from between conveyor belts 62 and 63 of the transfer conveyor 61 will be admitted between an adjacent pair of paddles such as the pair marked 81 and 81' for being carried on the chain around to the output side of the inverter as has happened to the diaper marked 85. In other words, a diaper such as the one between paddles 81 and 81' enters the inverter 80 with its folded edge leading and its unfolded or open edges trailing and, after being operated on by the inverter, the diaper will have its open edges leading and its folded edge trailing as is the case with the diaper marked 85.

The paddle carrying chain 84 and its mate 84' run on coaxial pairs of idler sprockets such as those marked 86 and 87 and paddle chain 84 and its counterpart 84' (see FIG. 3) are driven by sprockets on a driven shaft 88. As can be seen in FIGS. 1 and 3, shaft 88 has a sprocket 89 that is driven by chain 75 which runs back to gear box 48.

FIG. 1 also shows one of a pair of small sprockets 90 and 90' which are fastened to driven shaft 88 and are used to drive a pair of closed loop dog carrying chains one of which chains is visible in FIG. 1 and is marked 91. Chain 91 and its counterpart 91' (see FIG. 3) carry L-shaped dogs or lugs which are pivotally connected to the chain and are exemplified by the lug marked 92. These laterally spaced apart lugs run along the side edges of a pair of paddles such as the pair holding the diaper marked 85, and propel the inverted diaper along the top surface of a narrow stationary metal band 93. Chains 91 and 91' run on laterally spaced apart pairs of idler sprockets such as those marked 94, 95 and 96. Band 93 terminates in a horizontal surface 101 which constitutes part of a diaper receiving table. Immediately above the horizontal surface 101 of band 93 is another horizontal surface 102 of another stationary band or guide 103. It will be evident that a diaper which has been inverted, such as the one marked 97, will arrive under band 102 at the same time as another diaper 98, which has not been inverted, will arrive so that the outgoing diapers will be stacked in pairs with their folded edges on opposite sides of the stack and they will be separated by the horizontal part 102 of band or guide 103. The top diaper 98 is prevented from unfolding at this time by a flexible and weighted strip of material 99. Because of the superimposed diapers being simultaneously engaged by the dogs 92 on chain 91, the diapers will ultimately leave the flat horizontal surfaces 101 and 102 and will become superimposed directly on each other as are the pair of diapers marked 13 and 14. The diapers are then transferred to output conveyor 15 in pairs for being processed by the packaging machine, not shown. The L-shaped dogs 92 are maintained in an upright position when they are transporting a diaper by virtue of running on a guide plate 100.

The arrangement of the parts involved in orbiting the paddles and in driving the dog carrying chains are shown in greater detail in FIG. 3 which is a partial section taken on the line 3—3 in FIG. 1.

In FIG. 3 the drive shaft 88 for the dog carrying chains 91 and 91' is journaled in opposite bearings 106 and 107 which are carried on stationary mounting plates 108 and 109. At the left, shaft 88 is coupled to its extension 88' through an overload clutch 110. Shaft 88' has a pinion 111 fixed on it and it is further journaled in a bearing 112 on a mounting plate 113. The laterally spaced apart sprockets 90 and 90' for dog chains 91 and 91' are fixed on shaft 88' and one pair of dogs or lugs 92 and 92' which are hingedly connected to the respective chains are shown in this figure. The laterally spaced apart pair of sprockets 114 and 115 for the paddle carrying chains 84 and 84' are freely rotatable on shaft 88' as they must be in order to permit the dog carrying chains 91 and 91' to run at a different speed than the paddle carrying chains 84 and 84'. Referring back to FIG. 1, the axis of shaft 88 can be seen to constitute a common center for the dog and paddle chains so that the diaper product leaves the paddle and goes to the dog chain conveyor around this axis. This effectuates a smooth transfer from the inverter 80 to the dog chain conveyor.

FIG. 3 shows that one of the pairs of sprockets 116 and 117 for the paddle carrying chains 84 and 84' are fastened to a shaft 118 which is journaled in bearings 119 and 120 mounted on fixed plates 109 and 113. Here it will be evident that the paddle carrying chains 84 and 84' are located inside of the dog carrying chains 90 and 90' to permit the dogs 92 to carrying the diapers off the paddles by engaging the diapers near their side edges. One of the connectors 127 for connecting paddles 81 to chains 84 and 84' is shown. In FIG. 3, shaft 118 for the paddle chains is driven indirectly from pinion 111 on shaft 88' through a gear train. Pinion 111 drives a cluster gear and meshes with gear 121. Clustered with 121 is gear 123 which, in turn, meshes and drives 124 which is fastened to, and thus drives, shaft 118. Proper phasing is necessary to assure that a diaper pad such as 98 in FIG. 1 whose fold is leading arrives in coincidence on the receiving table and congruently with a diaper such as 97 which has been inverted.

Although the main features of the new apparatus have been described in considerable detail, such description is intended to be illustrative rather than limiting, for the new concepts of the apparatus may be variously embodied and the scope of the invention is to be limited only be interpretation of the claims which follow.

I claim:

1. Apparatus for inverting alternate pads such as diapers in a succession of pads which are folded in the same direction to enable stacking them with folded and open edges of alternate pads on opposite sides of the stack, said machine comprising:

pad sorting means for receiving the succession of pads while they are still folded in the same direction and for discharging them in alternate succession into first and second lanes, a pad receiving station spaced from said sorting means, power driven first conveyor belt means disposed in the first lane for receiving alternate pads which are discharged from said sorting means and for transporting said pads successively to said pad receiving station, interfacing power driven second conveyor means disposed in said second lane for receiving alternate pads which are discharged from said sorting means and for transporting and discharging said pads, inverter means operative to receive pads discharged from said second conveyor means and to invert them so their folded edges and open edges are opposite from corresponding edges of the pads in said first lane, said inverter means comprising power driven closed loop chain means and sprockets on which said chain means run, a series of translatable paddles disposed in spaced relation along said chain means and having their corresponding ends pivotally connected to said chain means and opposite corresponding free ends projecting away from said chain means to provide spaces for receiving between them pads which are discharged in said second lane from said second conveyor means, conveyor means for advancing said pads from said inverter means to said receiving station comprising power driven closed loop chain means having an inclined portion and a plurality of sprockets on which said chain means run, said chain means having a series of dogs disposed in spaced relation along it with corresponding ends of the dogs pivotally connected to said chain means, said dogs being translatable with said chain means for removing inverted pads from said paddles when the paddles become parallel to said inclined portion of the chain and for transporting said pads to said receiving station above the inverter, a shaft on which one of the sprockets for said paddle carrying chain and one of the sprockets for said dog carrying chain is fastened, the axis of said shaft being a common center for the paddle carrying and dog carrying chains such that a pair of paddles holding a pad extends radially from said common center and is disposed in alignment with said inclined portion of the dog carrying chain when its dogs removes a pad from said paddles, and, means for removing superimposed alternately folded pads from said receiving station simultaneously.

* * * * *